United States Patent [19]

Sage, Jr. et al.

[11] Patent Number: 5,735,810
[45] Date of Patent: Apr. 7, 1998

[54] DEVICE FOR THE IONTOPHORETIC ADMINISTRATION OF BISPHOSPHONATES

[75] Inventors: Burton H. Sage, Jr., Raleigh, N.C.; Philip G. Green, Cliffside Park, N.J.

[73] Assignee: Becton Dickinson and Company, Franklin Lakes, N.J.

[21] Appl. No.: 708,332

[22] Filed: Sep. 4, 1996

Related U.S. Application Data

[63] Continuation-in-part of Ser. No. 665,181, Jun. 14, 1996.
[51] Int. Cl.$^6$ .................................................... A61N 1/30
[52] U.S. Cl. ........................................... 604/20; 607/51
[58] Field of Search ........................... 604/19–20, 289, 604/304, 890.1; 607/2–3, 50–51, 115

[56] References Cited

U.S. PATENT DOCUMENTS 5,376,107  12/1994  Inagi et al. ................................ 604/20

FOREIGN PATENT DOCUMENTS 0092101  4/1996  Japan.
9528145  10/1995  WIPO.

OTHER PUBLICATIONS

Landman, J.O., et al., "Recovery of Serum Calcium Concentrations following Acute Hypocalcemia in Patients with Osteoporosis . . ." J. Clin. Endocrin. Met. 80(2)524–8(1995).

Dawson–Hughes, B. et al. "A controlled trial of the effect of calcium supplementation on bone density . . ." New Eng. J. Med. Sep. 27, 1990, 323(13)878–883.

Watts, N.B., Blevins, L.S.Jr., "Endocrinology" JAMA Jun. 19, 1996 275(23) 1806–1807.

Pak, C.Y.C.,et al., "Treatment of Postmenopausal Osteoporosis with Slow Release Sodium Fluoride," Annals of Internal Medicine, Sep. 15, 1995,123(6)401–8.

Storm, Thomas, et al. Effect of Intermittent Cyclical Etidronate Therapy on Bone Mass . . . , 322 New Eng. Jnl. Med. 1265 (1990).

*Primary Examiner*—Michael Powell Buiz
*Assistant Examiner*—Ellen S. Tao
*Attorney, Agent, or Firm*—Susan A. Capello

[57] ABSTRACT

The present invention relates to a method and device for the iontophoretic delivery of a therapeutic dose range of bisphosphonate to be delivered to a patient over a period of time to prevent the onset for advancement of osteoporosis and other metabolic bone diseases for a selected period of time.

4 Claims, 3 Drawing Sheets

FIG-1 4c. 0.64mg/mL BISPHOSPHONATE A pH 6.8

DEVICE FOR THE IONTOPHORETIC ADMINISTRATION OF BISPHOSPHONATES

This Application is a Continuation-In-Part of application Ser. No. 08/665,181 filed on Jun. 14, 1996.

FIELD OF INVENTION

The present invention relates to a non-invasive method and apparatus for preventing the onset and advancement of osteoporosis and other metabolic bone diseases through the intermittent iontophoretic administration of a bisphosphonate.

BACKGROUND OF THE INVENTION

Iontophoretic drug delivery systems, have, in recent years, become an increasingly important means of administering drugs.

Presently there are two types of transdermal drug delivery systems, i.e., passive and iontophoretic. Passive patch systems deliver small and relatively lipophilic drugs through the skin of the patient by diffusion, an example of which would involve the application of a narcotic analgesic patch to provide pain relief. Iontophoresis systems, on the other hand, deliver drug through the skin of the patient through the application of an electromotive force (iontophoresis) to drive ionizable substances (medicament) into the skin so that they can be absorbed by adjacent tissues and blood vessels. Iontophoresis, therefore, allows charged and hydrophilic drugs to be transported across the skin which are poorly deliverable through passive diffusion. Transdermal systems offer advantages clearly not achievable by other modes of administration, such as hypodermic injection which has the associated problem of pain, risk of infection and trauma to the patient. Iontophoresis also has advantages over oral administration in that introduction of the drug through the gastrointestinal tract may result in inactivation of the medicament, food interactions, first pass hepatic metabolism and gastrointestinal side effects.

Conventional iontophoretic devices, such as those described in U.S. Pat. Nos. 4,820,263 (Spevak, et al.), 4,927,408 (Hank, et al.) and 5,084,008 (Phipps), the disclosures of which are hereby incorporated by reference, provide for delivery of a drug or medicament transdermally through iontophoresis. Basically, conventional iontophoretic devices consist of a power source connected to two electrodes, an anode and a cathode, which are individually in ionic contact with an electrolyte or drug reservoir which is in contact with the skin to be treated by the iontophoretic device. When the current is turned on, electrical energy is used to assist in the transport of ionic molecules into the body through the skin, via ionic conduction.

Osteoporosis is a metabolic skeletal disorder wherein bone strength decreases and risk of bone fracture increases. Bone strength is maintained by a continual process of bone resorption and bone regeneration. Osteoporosis results when bone resorption occurs at a faster rate than bone regeneration. During the first three decades of life, bone regeneration exceeds bone resorption, resulting in maximum bone strength in the fourth decade of life. After the fourth decade of life, and especially for women, after menopause, bone resorption exceeds bone regeneration, resulting in an ever increasing risk of bone fracture with age. Osteoporosis may also be observed in patients who are undergoing prolonged treatment with adrenal corticosteroids, who lead sedentary lifestyles, who suffer from chronic renal disease, and malnutrition. In about 10% of the population, the risk of at least one fracture is high. Osteoporosis is a major public health problem, in the U.S., osteoporosis affects 25 million people, resulting in 1.3 million fractures each year, including more than 500,000 spine, 250,000 hip and 240,000 wrist fractures, and costs the nation in excess of $10 billion.

This disorder is asymptomatic, with the result that the individual at risk is unaware of his/her condition. Women are roughly four times more susceptible than men. Approximately 25% of the population will suffer the affects of osteoporosis either as one or more bone fractures or as significant bone pain. This enormous patient population is at once both a major pharmaceutical opportunity and a health care funding nightmare.

There are several compelling needs in the prevention and treatment of osteoporosis. One is in the area of prevention of the onset of osteoporosis and another is in the area of prevention of the advancement of osteoporosis. For both of these needs calcium and vitamin D supplements are effective in slowing the loss of bone strength, but the end result is only delay in the onset of symptomatic disease. Treatment with estrogen or calcitonin is claimed to be more effective than treatment with vitamin D and calcium, however, compliance is poor and these medicines are expensive.

An alternative medicament is bisphosphonate. This class of drug acts directly on the bone to dramatically reduce bone resorption, thereby stabilizing bone mineral density. However, bisphosphonates have very low oral bioavailability which may lead to highly variable dosing. Also, the low oral bioavailability varies with food, calcium levels, plus a number of other factors. The bisphosphonate oral dosing regimen is also somewhat complicated in that the drug must be taken daily e.g. in the case of Fosamax® (Alendronate), thirty (30) minutes to one (1) hour prior to breakfast and with large amounts of water, and in addition, the patient should not lie down for thirty (30) minutes after taking the drug. The drug cannot be prescribed for patients with abnormalities of the esophagus and/or the inability to stand or sit upright for at least thirty (30) minutes. Such issues may result in certain excluded patents and poor compliance for a chronic asymptomatic disease such as osteoporosis.

Bisphosphonates have a strong affinity for calcium and are, therefore, strongly bound to bone for extended period (years). Consequently, bisphosphonates could be given in higher than typical daily doses to patients for treatment of osteoporosis and other bone related disorders at intervals greater than a day (e.g. twice weekly, weekly, monthly, bi-monthly, tri-monthly or once every six months). Short intermittent i.v. infusion of the bisphosphonates pamidronate (Aredia®) and endronate (Didronel®), which have been shown to be efficacious in patients suffering from Paget's disease and hypercalcaemia associated malignancy. Medical research has also found that bisphosphonates when administered over several hours through an intravenous infusion provide the patient with pharmacological effects which may last several weeks, as reported by D. Thiebaud, et al. at the Third International Symposium Osteoporosis, entitled: "2 Years Effectiveness of Intravenous Pamidronate (APD) versus Oral Fluoride in Post menopausal Osteoporosis" the disclosure of which is incorporated herein by reference. Most recently it has been reported by P. Filipponi, et al in the Journal of Bone and Mineral Research, vol. 10, Nov. 5, 1995, in an article entitled "Cyclical Clodronate is Effective in Preventing Postmenopausal Bone Loss: A Comparative Study with Transcutaneous Hormone Replacement Therapy", that 200 mg of clodronate administered intravenously over a four (4) hour period once a month, resulted in a drop in total bone mineral density of 0.67%±0.84 as compared to the control change of more than 7%, the disclosure of which is herein incorporated by reference. However, patient compliance, with respect to receiving an i.v. infusion over several hours every few weeks, is likely to be poor and may lead to side effects. The procedure is also inconvenient and expensive. Passive transdermal delivery, although useful for delivering some drugs, is unlikely to be amenable to biphosphates since these drugs are charged and highly hydrophilic. The passage of hydrophilic molecules across the outermost layer of the skin, would be likely to be very low and highly variable. If a passive patch were possible, it would likely be large and need to be worn on a daily basis.

Applicants' invention has solved these problems. The present invention relates to an apparatus and method for preventing the onset and advancement of osteoporosis or other bone disorders by use of an iontophoretic administration of a bisphosphonate compound over several hours, at various dosing intervals. This avoids the side effects of oral dosing and the expense, side effects, and discomfort associated with administering an intravenous infusion over several hours.

Iontophoresis of a bisphosphonate has been demonstrated. In 1988, in an article entitled "Transdermal Delivery of Etidronate(EHDP) in the pig via iontophoresis," Journal of Membrane Science, 35(1988) 161–165, the authors show that the molecule can be delivered through the skin and that it remains biologically active since a large portion was located bound to bone. However, the authors clearly state that the selection of EHDP was as a model drug, and its use in the treatment of a disease state is not described. The article is directed to the feasibility of delivering EHDP transdermally with no hint or suggestion as to prolonged iontophoretic delivery providing extended term of protection. Further, the studied delivery episode is very short (90 min.), much shorter than the administration times claimed in this invention, and there is no suggestion that extended episodes of delivery might provide for extended intervals between administration episodes, which is the object of this invention. In addition, irritation of the skin was noted in the pig which would lead one away from using iontophoresis for longer term chronic administration of this class of drug.

None of the above patents or any prior art of which the inventors are aware describes a system or method intended for the iontophoretic delivery of bisphosphonates over a prolonged period of time to achieve a clinically beneficial, i.e. protective result.

The present invention provides a prevention strategy for the population at risk for osteoporosis. The iontophoretic patch can be administered at regular intervals by the physician or by the patient. The patch is worn by the patient for a set period of time and then after dosing at regular intervals (e.g. every week, every month or tri-monthly, etc.) removed and discarded. The preventative effects of the bisphosphonate lasts for an extended period of time.

SUMMARY OF THE INVENTION

One embodiment of the present invention provides for a method for preventing the onset or advancement of osteoporosis or other bone disorders in a patient. The method involves iontophoretically delivering to a patient an amount of bisphosphonate effective for preventing the onset or advancement of osteoporosis for a selected period of time after iontophoretic delivery.

Another embodiment of the present invention provides for an iontophoretic device for preventing the onset and advancement of osteoporosis or other bone disorders. The iontophoretic device has (a) a current distributing member;

(b) an ionized substance reservoir containing an ionized or ionizable substance, in electrical communication with the current distributing member and adapted to be placed in ionic communication with the epithelial surface; and wherein said ionized or ionizable substance is a bisphosphonate;

(c) an electrolyte reservoir containing an electrolyte, in electrical communication with an indifferent electrode and in ionic communication with an epithelial surface;

(d) an electrical power source in current delivering connection with the current distribution member and the electrolyte reservoir.

This device is capable of delivering an amount of bisphosphonate over a period of several hours which is effective for preventing the onset or advancement of osteoporosis.

DETAILED DESCRIPTION

Figure 1:
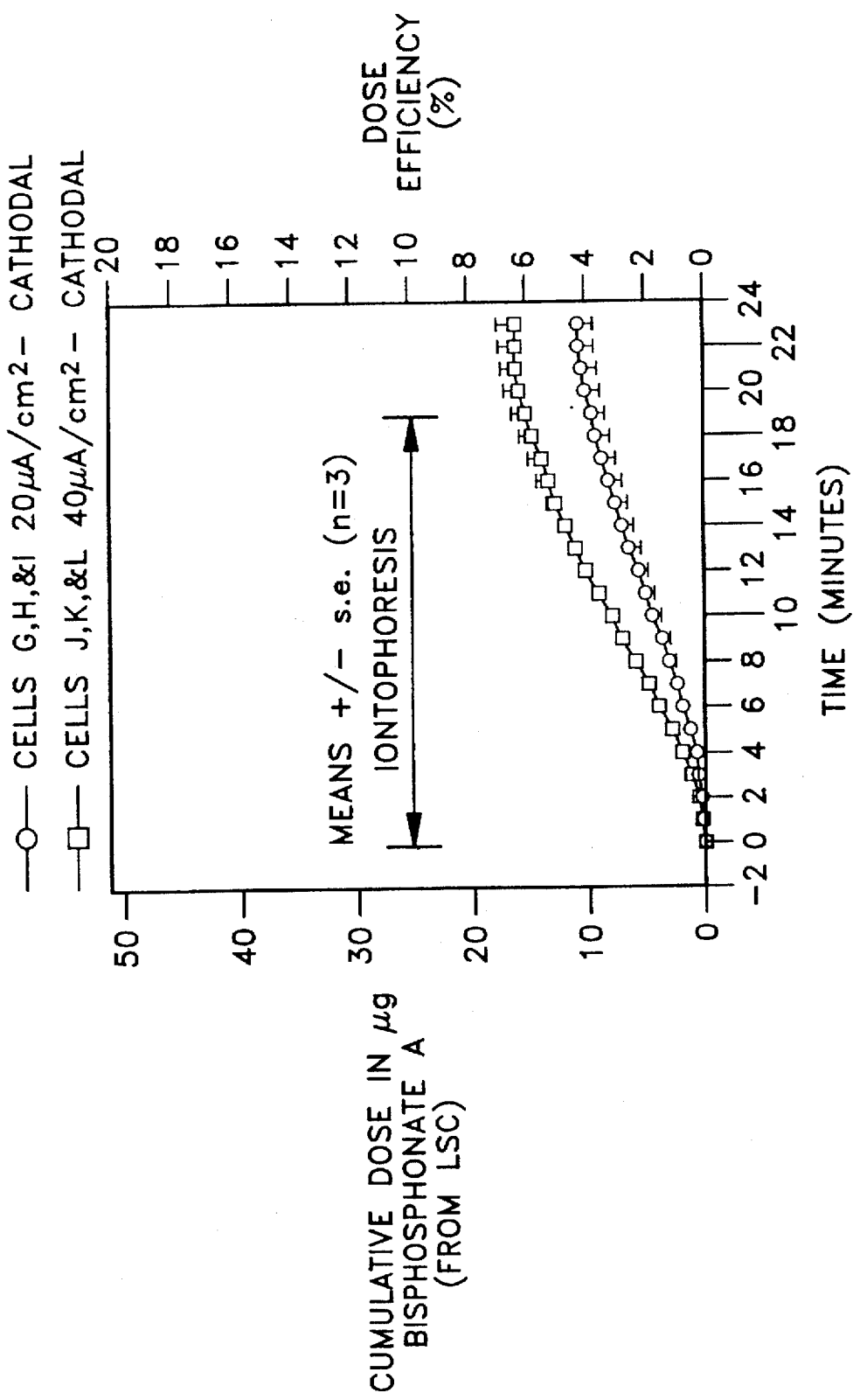
FIG. 1 depicts the effects of current density on cumulative doses of bisphosphonate A following iontophoretic delivery of bisphosphonate A over an eighteen (18) hour period across excised pig skin.

Preferably, the present invention should be used when the patient has reached menopause and where the menopausal symptoms are not being treated, as well as when the patient is suspected of being at risk for osteoporosis and there is little risk of fracture, as well as in patients suffering from other bone disorders, such as, Paget's disease, metabolic bone disorders and hypercalcaemia associated malignancy.

The present invention provides for a therapeutic dose range of the bisphosphonate to be iontophoretically delivered over a period of time, which should be effective for preventing the onset or advancement of osteoporosis for a selected period of time. The therapeutic ranges for several of the bisphosphonate compounds are known or available to those of ordinary skill in the art of treating osteoporosis.

Bisphosphonate compounds by way of example, and not limitation, include Etidronate, clodronate, pamidronate, alendronate, (6-amino-1-hydroxyhexylindene) bisphosphonate, tiludronate, risedronate, (3-(dimethylamino)-1-hydroxypropylidene)bis-phosphonate, (1-hydroxy3(methylpentylamino)propylidene)bis-phosphonate (BM 21.0955), (1-hydroxy-3-(1-pyrrolidinyl) propylidene)bis-phosphonate (EB-1053), other bisphosphonates known to those of ordinary skill in the art and mixtures thereof. Based on the known therapeutic ranges for the various bisphosphonate compounds, one of ordinary skill in the art should be able to designate the bisphosphonate as well as the therapeutic amount of that bisphosphonate which needs to be administered iontophoretically to prevent the onset or advancement of osteoporosis for an extended period of time after iontophoretic delivery. Thereby enabling the attending physician or the patient themselves to administer an iontophoretic patch which may be applied to the patient and activated for a period of time ranging from about four (4) hours to about forty-eight (48) hours which would be effective for preventing the onset or advancement of osteoporosis for a period of time ranging from one (1) week to about twice a year.

One embodiment of the present invention provides for a method for preventing the onset or advancement of osteoporosis in a patient. The method involves treating a patient with an amount of bisphosphonate effective for preventing the onset or advancement of osteoporosis for an extended period of time.

Another embodiment of the present invention provides for an iontophoretic device for preventing the onset and advancement of osteoporosis. The iontophoretic device has (a) a current distributing member;
(b) an ionized substance reservoir containing an ionized or ionizable substance, in electrical communication with the current distributing member and adapted to be placed in ionic communication with the epithelial surface;
wherein said ionized or ionizable substance is a bisphosphonate. This device is capable of delivering an amount of bisphosphonate effective for preventing the onset or advancement of osteoporosis for a selected period of time; and
(c) an electrolyte reservoir containing an electrolyte, in electrical communication with an indifferent electrode and in ionic communication with the epithelial surface;
(d) an electrical power source in current delivering connection with the current distribution member and the electrolyte reservoir.

The iontophoretic device of the present invention may by way of example and not limitation include the following component and materials.

Preferably, the method involves iontophoretically delivering to a patient, a chosen bisphosphonate compound for at least an four (4) hour period of time, to prevent the onset or advancement of osteoporosis or other bone disorders.

A. The Current Distributing Member (active electrode)

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes current without being eroded or depleted due to the distribution of current, and conducts current through the generating ions by either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

Additional types of materials useful as current distributing members according to the invention are disclosed in detail in an application entitled Low-Cost Electrodes for an Iontophoretic Device, by V. Reddy et al., Ser. No. 08/536,029, pending, filed on Sep. 29, 1995 (Attorney Docket P-3066), the disclosure of which is incorporated by reference herein.

The current distributing member may take any form known in the art, such as the form of a plate, foil layer, screen, wire, or dispersion of conductive particles embedded in a conductive matrix.

B. The Electrolyte Reservoir

1. Electrolytes

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having a concentration of less than 1 mole/liter (<1M), more preferably at about physiological concentration. Other electrolytes include salts of physiological ions including, but not limited to, potassium, ($K^+$), chloride ($Cl^-$), and phosphate ($PO_4^-$). The salt and its concentration may be selected as desired for particular applications. Other species may be selected by the skilled artisan for inclusion in the electrolyte reservoir. Such other reservoir species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays, polyoxyethylenes), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. The Ionized Substance (Drug) Reservoir

The reservoir structure of the iontophoretic apparatus of the invention further includes an ionized substance reservoir. The ionized substance reservoir must be in ionic communication with an epithelial surface.

The construction of the ionized substance reservoir must be consistent with the requirements for ionic communication with the epithelial surface and electrical communication with the current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant amount of hydrating material. In preferred embodiments, a cross-linked hydrogel in the electrolyte reservoir, because it inherently contains significant amounts of water, can serve as a water reservoir during iontophoresis.

It may be desirable to provide the solution of active ingredient with a buffer. The ion of the buffer of like charge to the drug ion should have low ionic mobility. The limiting ionic mobility of this ion is preferably no greater that $1 \times 10^{-4}$ cm$^2$/volt-sec.

Bisphosphonates are known to have a strong affinity for calcium and, therefore, formulation steps must be taken to avoid interaction of the drug and residual amounts of calcium in the reservoir. This may be achieved by the addition of agents capable of chelating calcium such as citrate salts, EDTA and other like chemicals.

D. The Ionizable Substance (Drug) for Iontophoretic Delivery

An ionic drug can be delivered from either the anode, the cathode, or both simultaneously. For example, if the ionic substance to be driven into the body is positively charged, then the positive electrode or anode will be the active electrode and the negative electrode or cathode will serve to complete the electrochemical circuit. Alternatively, if the ionic substance to be delivered is negatively charged, then the negative electrode will be the active electrode and the positive electrode will be the indifferent electrode. Since all bisphosphonates usually possess an overall negative charge at skin pH, the preferred embodiments of the present invention are directed to ionic drugs driven from the cathode of the iontophoretic device. However, it is to be understood that an anodic configuration may be used to drive positively charged chemical modifications of the bisphosphonate without departing from the spirit of the invention.

It is believed that this invention has utility in connection with the delivery of active ingredients within the broad class of bisphosphonates as well as chemical modifications of bisphosphonates.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized substance reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit.

Various types of electrodes may be employed such as is described in United States application entitled Low-Cost Electrodes for an Iontophoretic Device, by Reddy et al., Ser. No. 08/536,029, pending, filed Sep. 29, 1995.

The following bisphosphonates have been investigated for use in human bone disease: Etidronate, clodronate, Pamidronate, alendronate, (6-amino-1-hydroxyhexylindene) bis-phosphonate, tiludronate, risedronate, (3-(dimethylamino)-1-hydroxypropylidene) bis-phosphonate, (1-hydroxy-3(methylpentylamino)propylidene) bis-phosphonate (BM 21.0955) and (1-hydroxy-3-(1-pyrrolidinyl)propylidene)bis-phosphonate (EB-1053). As reported by H. Fleisch at the Third International Symposium Osteoporosis, entitled: "Use of Bisphosphonates in the Treatment of Osteoporosis" the disclosure of which is incorporated herein by reference. Other bisphosphonates have also been reported to be in various stages of clinical development. These include zoledronic acid, NE-10244, olpadronic acid, incadronic acid and YH-529.

Figure 3:
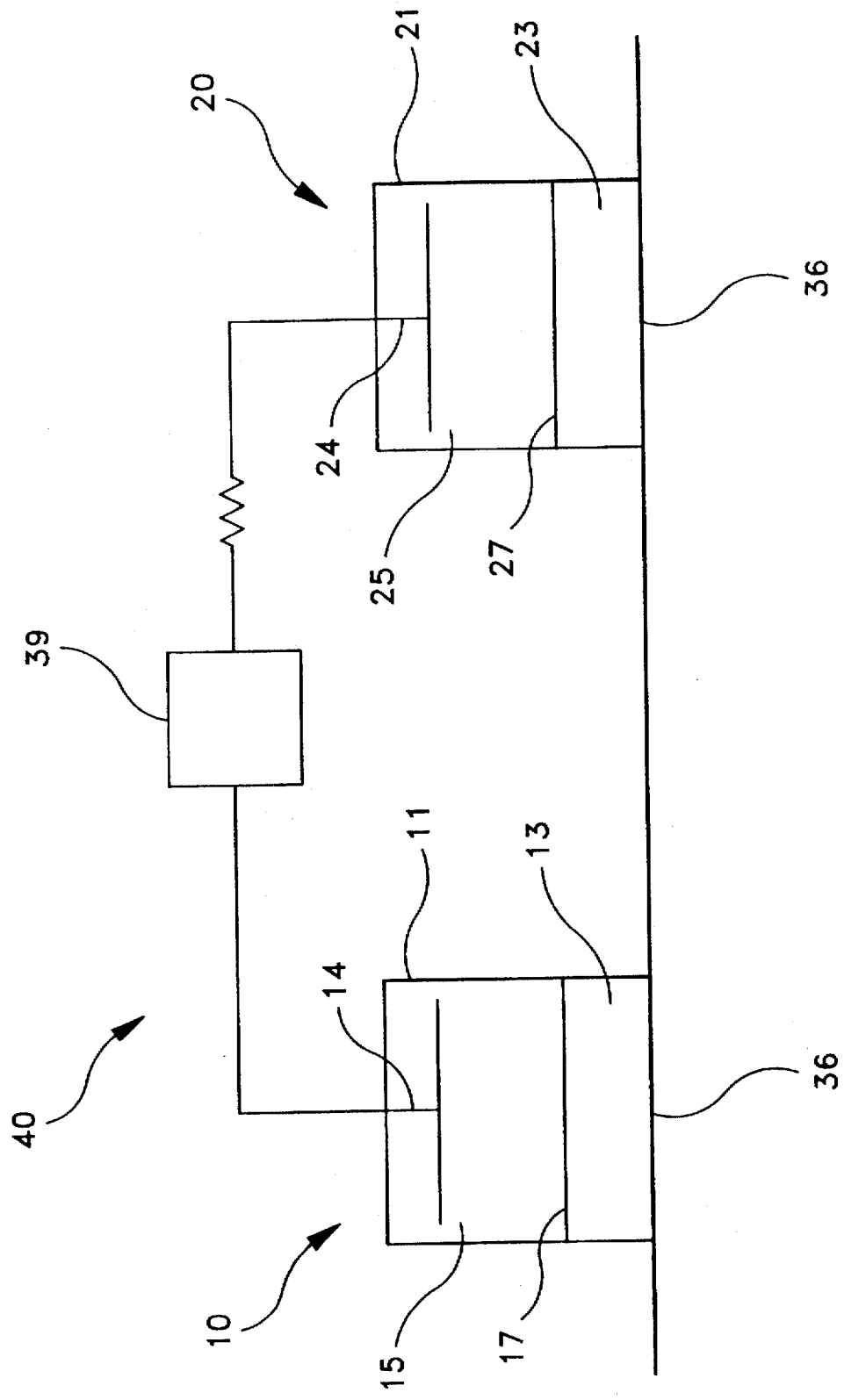
FIG. 3 depicts an embodiment of a device of the present invention.

As depicted in FIG. 3 an embodiment of the iontophoretic device of this invention 40 is configured as follows: an anode patch 10, having an anode electrode compartment 11 in ionic communication with a skin contacting compartment 13. The skin contacting compartment 13 and the anode electrode compartment 11 maybe separated by a compartment separation means (membrane) 17. The anode electrode compartment 11 also contains an anode 14 and an electrolyte (anolyte) 15. The skin contacting compartment is attached to the patient's skin 36. A cathode patch 20, having a cathode electrode compartment 21 in ionic communication with a skin contacting compartment 23. The skin contacting compartment 23 and the cathode electrode compartment 21 maybe separated by a compartment separation means (membrane) 27. The cathode electrode compartment 21 also contains an cathode 24 and an electrolyte (catholyte) 25. The skin contacting compartment is attached to the patient's skin 36.

While the present invention has been described in connection with iontophoresis, it should be appreciated that it may be used in connection with other principles of active introduction, i.e., motive forces. Accordingly, the invention is understood to be operative in connection with electrophoresis, which includes the movement of particles in an electric field toward one or the other electric pole (anode or cathode), and electroosmosis, which includes the transport of uncharged compounds due to the bulk migration of water induced by an electric field. Also it should be appreciated that the patient or subject may include humans as well as animals.

EXAMPLES

Experiment 1

Iontophoretic delivery of a bisphosphonate compound, having a negative charge and a molecular weight of approximately 300 daltons and hereinafter referred to as "bisphosphonate A", was carried out over an eighteen (18) hour period. An in-vitro model utilizing excised pig skin and providing for cathodal iontophoretic delivery of the C-14 radiolabeled bisphosphonate A was used to collect the data—presented in this example. The concentration of the bisphosphonate A in the patch was 0.64 mg/ml delivered iontophoretically for an 18 hour period of time. The standard iontophoretic device comprised of an anodal portion containing an electrolyte in ionic communication with an inactive or return electrode in contact with the excised skin, electrically connected to the anodal portion is a cathodal portion containing an ionized or ionizable bisphosphonate A in ionic communication with an active electrode, such cathodal portion also being in ionic communication with the excised skin. Both portions are in electrical communication with a power source. A current of 0.02 or 0.04 mA was run through the device. The cathodal portion is 2 $cm^2$ and was loaded with 256 μg of the bisphosphonate A. The system was maintained at a pH of 6.8. A total of six (6) cells were run, three (3) at 10 $\mu A/cm^2$ and three (3) 20 $\mu A/cm^2$.

The results are shown in FIG. 1, which depicts the cumulative dose of bisphosphonate A in mg delivered as a function of time (hour) over a 24 hour period. As depicted in FIG. 1, the data is consistently reproducible, the dosing was steady as indicated by the slope of the curve being relatively straight and as evidenced by the fact that cumulative dose of bisphosphonate A being delivered over most of the 24 hour time period was maintained between 10 and 20 mg; which is in the range of the effective therapeutic weekly dose level (7–19 μg) for bisphosphonate A.

Experiment 2

Figure 2:
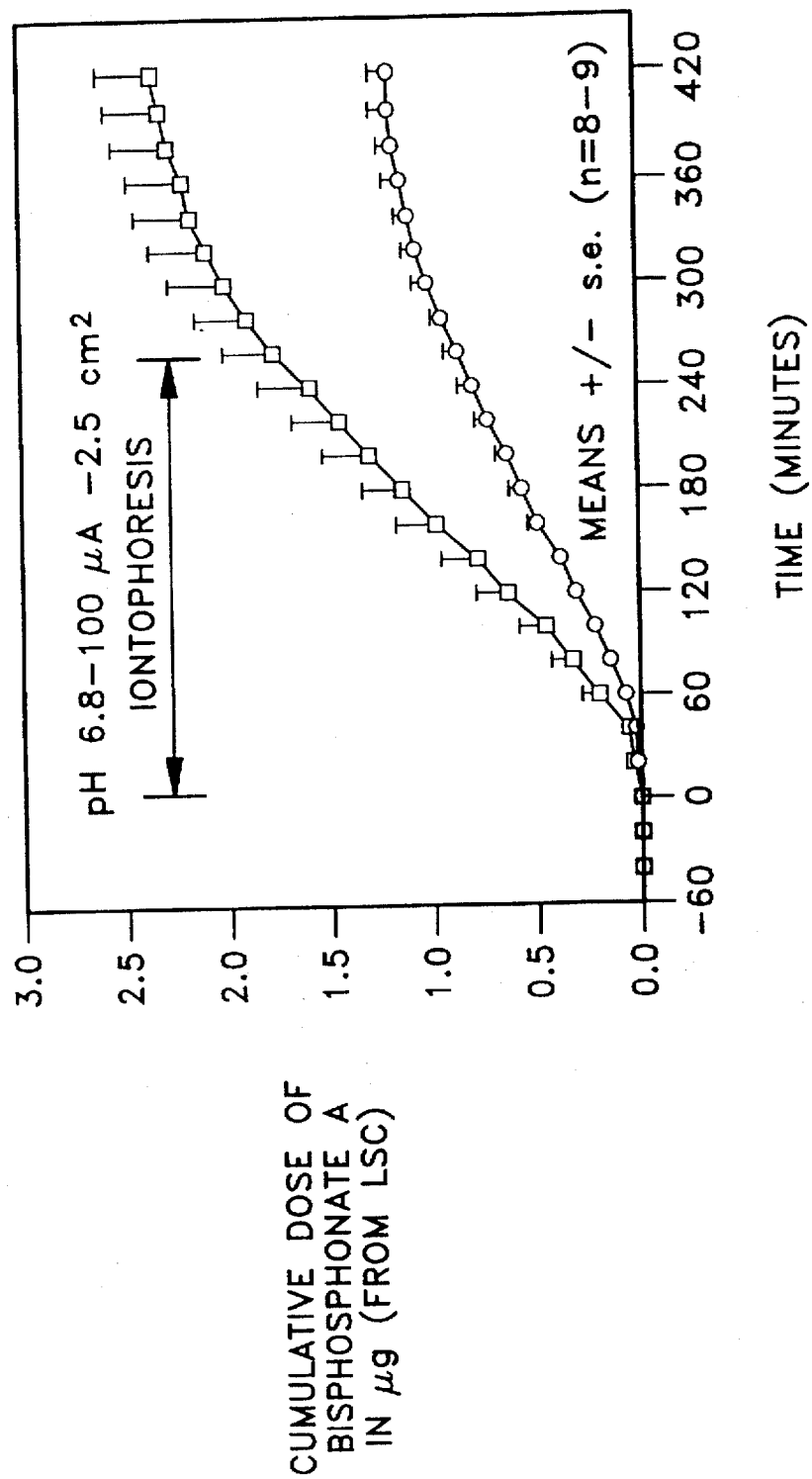
FIG. 2 depicts cumulative delivery of bisphosphonate A following iontophoretic delivery over a four (4) hour period across excised pig skin at two patch concentrations.

A further 4 h in-vitro study using bisphosphonate A was also carried out at lower concentrations of 0.08 and 0.16 mg/ml using 100 ua and a 2.5 $cm^2$ patch. The results are shown in FIG. 2 and indicate that the dose delivered of bisphosponate A is proportional to patch concentration of the bisphosphonate A. Again, a weekly dose of the bisphosphonate compound could be obtained using higher current and a large patch. Table 1 highlights the low variability in dosing resulting from iontophoretic delivery.

TABLE I

| bisphosphonate A Run No. | Dose (ug) |
|---|---|
| | 0.08 mg/ml |
| 1 | 1.8 |
| 2 | 1.1 |
| 3 | 1.3 |
| 4 | 1.3 |
| 5 | 1.2 |
| 6 | 1.3 |
| 7 | 0.8 |
| 8 | 1.2 |
| 9 | 0.7 |
| N | 9 |
| Mean | 1.21 |
| S.D.(samp) | 0.32 |
| C.V.(%) | 26.5 |
| | 0.16 mg/ml |
| 10 | 2.2 |
| 11 | 3.9 |
| 12 | 1.2 |
| 13 | 2.4 |
| 14 | 2.7 |
| 15 | 1.8 |
| 16 | 2.1 |
| 17 | 2.6 |
| N | 8 |
| Mean | 2.35 |
| S.D.(samp) | 0.78 |
| C.V.(%) | 33.4 |

Experiment 3

In Vivo Irritation Experiments—Method

The irritation experiments involved a variety of patches and formulations. In each case, the patches were loaded with drug solution immediately before application to the skin of the animals. Areas of use on the animals were clipped to remove fur just prior to use. For the rabbit experiments, the patches were overwrapped with an adhesive, elastic wrap to hold the patches in place. Separate constant current power supplies were provided for each iontophoresis patch system. In rabbit experiments either one or two patch systems were applied to each individual. For the pigs, as many as 10 separate patch systems were applied to the back of a single individual. Rabbits were restrained in stainless steel restrainers and the pigs were anesthetized with isoflurane during the dosing. Visual scoring (Draize) was used to assess the acute skin responses on a daily basis following the dosing.

Pig Study

A single anesthetized pig was dosed on the back for 4 hours with 10 sets of iontophoresis patches and 3 passive patches. All active areas were 2.5 cm$^2$. Factors included bisphosphonate A concentration (0.08, 0.16, and 0.32 mg/ml); current (50 or 100 µA) and pH (4.3 or 6.8). At 0.08 and 0.16 mg/ml, scores for erythema and edema were never more than 1. At bisphosphonate A concentration of 0.32 mg/ml, scabbing (erythema=4) was observed in ¾ runs. Effects of pH was not discernible.

Rabbit Study

A factorial design was used with 4 replicate runs for the 12 possible combinations of factor settings for bisphosphonate A concentration (0.04, 0.08 and 0.24 mg/ml); current (100 or 400 µA) and time (2 or 4 h). The pH was kept constant at 6.8. All active areas were 2.5 cm$^2$. Irritation increased with increasing concentration of bisphosphonate A and higher current. The effect of time, however, was not discernible. Irritation levels ranged from very mild, with all daily average scores <1, to moderate, with daily averages for erythema and edema at 2.5–3 and 1.5, respectively. Scabbing also resulted from the more severe treatments.

The delivery data shows that, at a variety of operating conditions, transdermal iontophoresis of bisphosphonate A is very effective. Control of delivery is possible with several factors, including drug concentration current and the duration of iontophoresis. Therapeutic doses of bisphosphonate A are easily provided by 4 hour episodes with acceptable active patch areas at low current density and low bisphosphonate A concentrations.

The irritation studies showed that skin responses associated with iontophoretic delivery of bisphosphonate A in rabbits and pigs increase in frequency of occurrence and severity with both drug concentration and current density. These two factors play major roles in determining drug flux (µg/cm$^2$/h), and for a set time, determine the dose density (µg/cm$^2$). Thus, the irritation is likely flux or dose density dependent.

The once-a-day dose target of 2.5 µg is delivered by a small active area, 2.5 cm$^2$, with a drug concentration of 0.16 mg/ml and 4 hours of iontophoresis at a current density of 40 µA/cm$^2$. With a larger active area, 8 cm$^2$, and 0.16 mg/ml at the same current density and duration, the dose is expected to be 7.5 µg, close to 3× the dose from the smaller patch and within the once-a-week dose target range of 7–19 µg.

The irritation observed in rabbits and pigs for these once-a-week and once-a-day dosing conditions is considered mild to moderate. For the same condition, the irritation in the pigs appeared milder than that seen in rabbits.

The study has shown that therapeutic doses of bisphosphonate A are readily delivered with transdermal iontophoresis. With low current density and low drug concentrations, once-a-week dosing is achievable with a larger area, 8 cm$^2$ active surface skin patch. Mild to moderate acute skin irritation is associated with the iontophoretic dosing of bisphosphonate A in rabbits and pigs with these conditions.

We claim:

1. An iontophoretic device for preventing the onset and advancement of osteoporosis comprising:

(a) a current distributing member;

(b) an ionized substance reservoir containing an ionized or ionizable substance, in electrical communication with the current distributing member and adapted to be placed in ionic communication with an epithelial surface, wherein said ionized or ionizable substance is a bisphosphonate; and (c) an electrolyte reservoir containing an electrolyte, in electrical communication with an indifferent electrode and adapted to be placed in ionic communication with an epithelial surface wherein said device is capable of delivering an amount of bisphosphonate effective for preventing the onset or advancement of osteoporosis for an extended period of time;

(d) an electrical power source in current delivering connection with the current distributing member and the electrolyte reservoir;

wherein the effective amount of bisphosphonate is delivered over a period of from about four (4) hours to about forty-eight (48) hours, at intervals of from about once a week and up to about twice a year;

wherein the bisphosphonate administered iontophoretically is selected from the group consisting of: Etidronate, clodronate, pamidronate, alendronate, (6-amino-1-hydroxyhexylindene)bis-phosphonate, tiludronate, risedronate, (3-(dimethylamino)-1-hydroxypropylidene)bis-phosphonate, (1-hydroxy-3 (methylpentylamino) propylidene)bis-phosphonate (BM 21.0955), (1-hydroxy-3-(1-pyrrolidinyl) propylidene)bis-phosphonate (EB-1053) zoledronic acid, olpadronic acid, incadronic acid, NE-10244, YH-529 and mixtures thereof; and wherein the ionized substance reservoir further comprises an agent capable of chelating calcium in an amount effective to prevent interaction between the bisphosphonate and any residual calcium in the ionized substance reservoir.

2. The device of claim 1 wherein the agent capable of chelating calcium is citrate salts.

3. The device of claim 2 wherein the citrate salt is citric acid.

4. The device of claim 1 wherein the agent capable of chelating calcium is EDTA.

* * * * *